United States Patent [19]

Teramoto

[11] Patent Number: 4,967,601
[45] Date of Patent: Nov. 6, 1990

[54] VISCOELASTICITY MEASURING APPARATUS

[75] Inventor: Yoshihiko Teramoto, Tokyo, Japan

[73] Assignee: Seiko Instruments, Tokyo, Japan

[21] Appl. No.: 388,830

[22] Filed: Aug. 3, 1989

[30] Foreign Application Priority Data

Aug. 5, 1988 [JP] Japan ................. 63-195809

[51] Int. Cl.⁵ .............................. G01D 7/02
[52] U.S. Cl. ...................................... 73/789
[58] Field of Search .................. 73/788–793, 73/812, 849, 852, 853

[56] References Cited

U.S. PATENT DOCUMENTS 4,019,365 4/1977 Woo ..................... 73/791
4,033,181 7/1977 Oeser .................... 73/822

*Primary Examiner*—Robert Raevis
*Attorney, Agent, or Firm*—Spensley Horn Jubas & Lubitz

[57] ABSTRACT

A viscoelastsicity measuring apparatus which includes a pair of sample holders, a sample clamping chuck, a detecting rod, a detecting rod support, a displacement detector, a force generator, a sine-wave generator, an amplifier and a heat source for heating the sample and which operates such that a sine-wave stress is induced in the sample and a strain generated in the sample due to the stress is detected so that the modulus of complex elasticity as a characteristic value of the viscoelasticity of the sample is measured on the basis of the amplitude of the stress and the phase difference between the stress and strain. Further, the sample holders are made resilient so that they can move in a direction normal to the sine-wave stress without loss while the extent of their movement in the direction of the stress is made so small as to be negligible, whereby any deformation of the sample due to a thermal expansion of the sample by heating is eliminated in the direction of the stress and strain detection, thereby improving the viscoelasticity measurement accuracy at a temperature different from the temperature at which the sample is set.

5 Claims, 1 Drawing Sheet

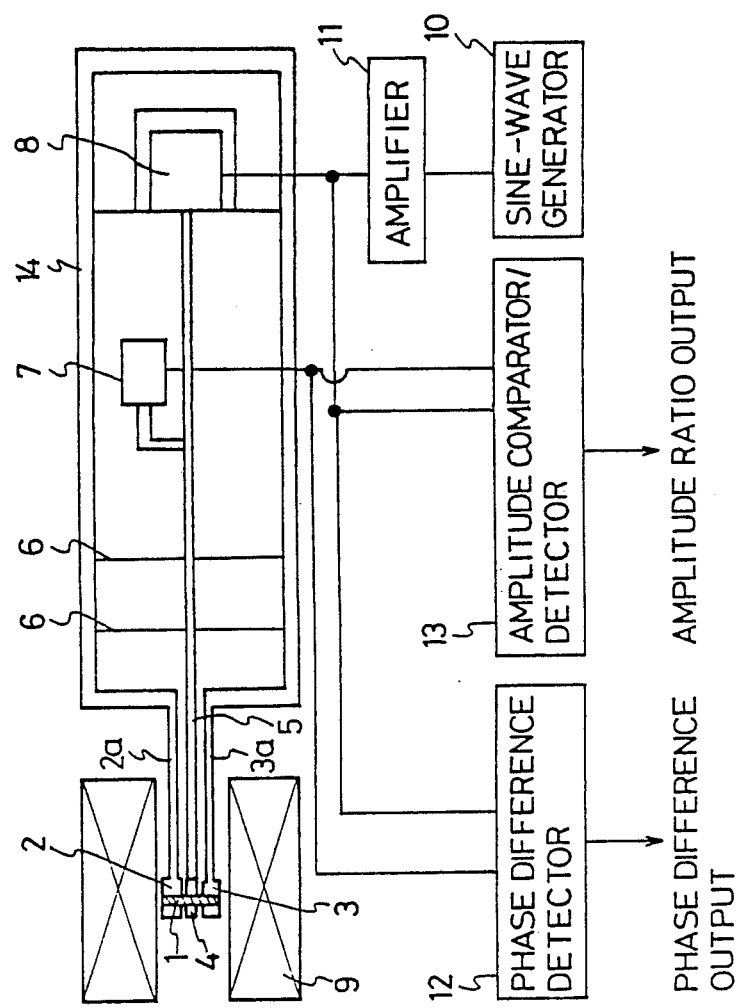

VISCOELASTICITY MEASURING APPARATUS

BACKGROUND OF THE INVENTION

The present invention relates to dynamic viscoelasticity measuring apparatus for detecting the dependence of the viscoelastic property of a material on temperature, time or frequency, and more particularly to apparatus of this type that can improve the accuracy of measured data.

In conventional apparatus of the above-described type, use has been made of sample holders which are held stationary to prevent both ends of the sample from moving in any direction.

However, the above-mentioned prior art technique has exhibited certain problems because of the fact that where the temperature dependence of the modulus of complex elasticity of a sample having a high coefficient of thermal expansion is measured, since both ends of the sample are held stationary, the thermal expansion of the sample is restricted at its ends so that the central portion of the sample deforms in the stress and strain detecting direction, in the direction normal to the detecting direction, and in the direction normal to the longitudinal direction of the sample. The following specific problems occur:

(1) The shape of a sample required for a basic formula to calculate the modulus of complex elasticity of the sample is a parallelepipedon or a column so that if the sample bends due to its thermal expansion, a measurement error will result; and (2) As the sample deforms in the stress and strain detecting direction, the central position of the strain detection shifts with the thermal expansion of the sample and this requires the provision of a complicated mechanism for detecting the central strain detecting position.

SUMMARY OF THE INVENTION

It is an object of the present invention to eliminate errors caused by thermal expansion of a sample in the measurement of viscoelasticity by a viscoelasticity measuring apparatus.

The above and other objects are achieved, according to the invention by: a pair of sample holders each of which holds a respective end of a sample in such a manner that the sample is allowed to move in the direction of a line extending through the sample ends due to elastic deformation of each of the holders but is prohibited from moving in the stress and strain detecting direction; a sample clamping chuck; a detecting rod for holding the chuck; a support for supporting the detecting rod; a displacement detector fixed to a part of the detecting rod; a moveable means for adjusting the position of the displacement detector; a force generator arranged at one end of the detecting rod so as to apply a force on the sample; a sine-wave generator for generating a sine-wave force in the force generator; an amplifier for adjusting the amplitude of the sine-wave force; and a heat source for heating the sample.

BRIEF DESCRIPTION OF THE DRAWING

The sole FIGURE is partly a schematic block diagram and partly a simplified pictorial view of a viscoelasticity measuring apparatus according to one embodiment of the present invention.

DESCRIPTION OF THE PREFERRED EMBODIMENTS

One embodiment of the present invention will now be described in detail with reference to the accompanying drawing.

In the drawing, sample 1 is held via its ends by a pair of sample holders 2 and 3.

The sample holders 2 and 3 are elastically supported by the free ends of elastic arms 2a and 3a, respectively, whose other ends are fixed to, and supported by, a box 14.

Further, the sample 1 is clamped at its middle by a chuck 4 which is fixed to a detecting rod 5 which is elastically supported by a detecting rod support 6 and whose movement is limited to a single straight line direction along the rod axis. In addition, a part of the detecting rod 5 is attached to a displacement detector 7 so as to detect the position of the rod 5 relative to the box 14. To the end of detecting rod 5 remote from sample 1 there is fixed an electrically driven force generator, or transducer, 8. A heat source 9 is disposed around the sample 1 so as to establish a suitable temperature environment for the sample.

A sine-wave generator 10 produces a sine-wave output signal which is applied to the force generator 8 after the amplitude of the output signal has been controlled by an amplifier 11.

The output of the amplifier 11 is also sent to a phase difference detector 12 and an amplitude comparator/detector 13 so that detector 13 generates an amplitude ratio signal and detector 12 generates a phase difference signal. As is well known, the two signals (i.e., the amplitude ratio signal and phase difference signal) have magnitudes expressing the viscoelastic characteristics of the sample with the former signal representing the modulus of reserved elasticity of the sample and the latter signal representing the sinusoidal loss thereof.

The operation of the apparatus of the present invention will now be described. The sample 1, the sample holders 2 and 3, the chuck 4 and a part of the detecting rod 5 are first heated by heat from the heat source 9. As a result of the heating, the sample holders 2 and 3 are forced away from one another by the sample 1 as the latter thermally expands, holders 2 and 3 being displaced by an amount sufficient to meet the thermal expansion of the sample 1 while continuing to hold the sample 1. This movement of holders 2 and 3 is made possible by the bending characteristics of arms 2a and 3a. Accordingly, the sample 1 does not deform in a direction parallel to the detecting rod 5 but deforms only in the direction of a line extending through both ends of the sample 1 (i.e., the direction normal to the detecting rod) and keeps its parallelepipedonal or columnar shape.

Then, the amplitude of the sine waves outputted from sine-wave generator 10 is adjusted by amplifier 11 whose output is in turn applied to force generator 8 and the force generated in force generator 8 is transmitted along the axis of rod 5 to generate a stress in sample 1, via chuck 4, which is perpendicular to a line extending through the ends of sample 1. The resulting strain generated in sample 1 at this time is detected by displacement detector 7 fixed to a part of detecting rod 5 and the modulus of complex elasticity of sample 1 is measured on the basis of the relationship of both the stress and strain being simultaneously detected, the stress being proportional to the amplitude of the output of amplifier 11.

Since the sample holders elastically deform in the direction of a line extending through both ends of the sample by being pressed by the sample, the sample keeps its parallelepipedonal or columnar shape even when subjected to temperature changes so that the purpose of measuring the modulus of complex elasticity of the sample at various temperatures can be attained.

As described above, the present invention has various effects. Firstly, since both ends of the sample are not held stationary but supported by the independent sample holders, respectively, the holders can move along the longitudinal direction of the sample so that the sample keeps its shape unchanged even when it is heated and the viscoelasticity thereof in a wide temperature range can be measured with accuracy. Secondly, since the sample is supported by holders which are on elastically deformable supports, the structure of the apparatus is simplified, allowing the arrangement around the sample to be made compact. Thirdly, the apparatus can meet the existing environmental conditions due to both thermal expansion and contraction of the sample.

This application relates to subject matter disclosed in Japanese Patent Application No. 63-195809, filed on Aug. 5, 1988, the disclosure of which is incorporated herein by reference.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. Apparatus for measuring the viscoelasticity of a sample which has two opposed ends, comprising: a pair of sample holders each for holding a respective end of the sample; elastically moveable support means supporting said holders for permitting said holders to move only along a line passing through the ends of the sample; a sample clamping chuck for clamping the sample at a location between its opposed ends; a detecting rod holding said chuck and having an axis extending transverse to the line passing through the ends of the sample when the sample is being held by said sample holders; means supporting said detecting rod for permitting said detecting rod to be displaced parallel to its axis; electrically driven force generating means coupled to one end of said detecting rod for applying a mechanical force to said detecting rod; sine wave signal generating means coupled to said force generating means for causing the mechanical force applied by said force generating to have a sinusoidal waveform; heating means for heating the sample to a selected temperature when the sample is being held by said sample holders; monitoring means mounted for monitoring movements of the sample when the sample is being held by said sample holders; and detecting means coupled to said signal generating means and said monitoring means for providing an indication of at least one relationship between the mechanical force applied by said detecting rod and the movements of the sample.

2. Apparatus as defined in claim 1 wherein said means supporting said detecting rod permit movements of said detecting rod substantially only parallel to its axis.

3. Apparatus as defined in claim 1 wherein said monitoring means include a movement sensor having an input element fixed to said detecting rod.

4. Apparatus as defined in claim 1 wherein said signal generating means comprise a sine wave signal generator having an output, and an amplifier having an input connected to said generator output and an output connected to said force generating means for applying a sine wave signal having a selected peak amplitude to said force generating means, said amplifier having an adjustable gain and said output of said amplifier being connected to said detecting means.

5. Apparatus as defined in claim 1 wherein said support means comprise two elongate, flexible arms each having two opposed ends and each extending parallel to the axis of said detecting rod, with one end of each said arm being fixed and the other end of each said arm carrying a respective sample holder.

* * * * *